US00PP22055P3

(12) United States Plant Patent
Deng et al.

(10) Patent No.: US PP22,055 P3
(45) Date of Patent: Aug. 2, 2011

(54) ***CALADIUM* PLANT NAMED 'UF331'**

(50) Latin Name: *Caladium×hortulanum*
Varietal Denomination: UF331

(75) Inventors: Zhanao Deng, Ellenton, FL (US); Brent Harbaugh, Bradenton, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/383,381

(22) Filed: Mar. 24, 2009

(65) Prior Publication Data

US 2010/0251442 P1 Sep. 30, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Susan B McCormick Ewoldt

(57) ABSTRACT

A new *Caladium* plant named 'UF331' particularly distinguished by its lance leaves with large dark green veins and white to red-purple interveinal areas, and demonstrated potential to produce attractive and sun-tolerant plants in outdoor sunny landscapes, and produce attractive pot plants when tubers are forced in containers, is disclosed.

1 Drawing Sheet

ACKNOWLEDGEMENT OF FEDERAL RESEARCH SUPPORT

Figure 1:
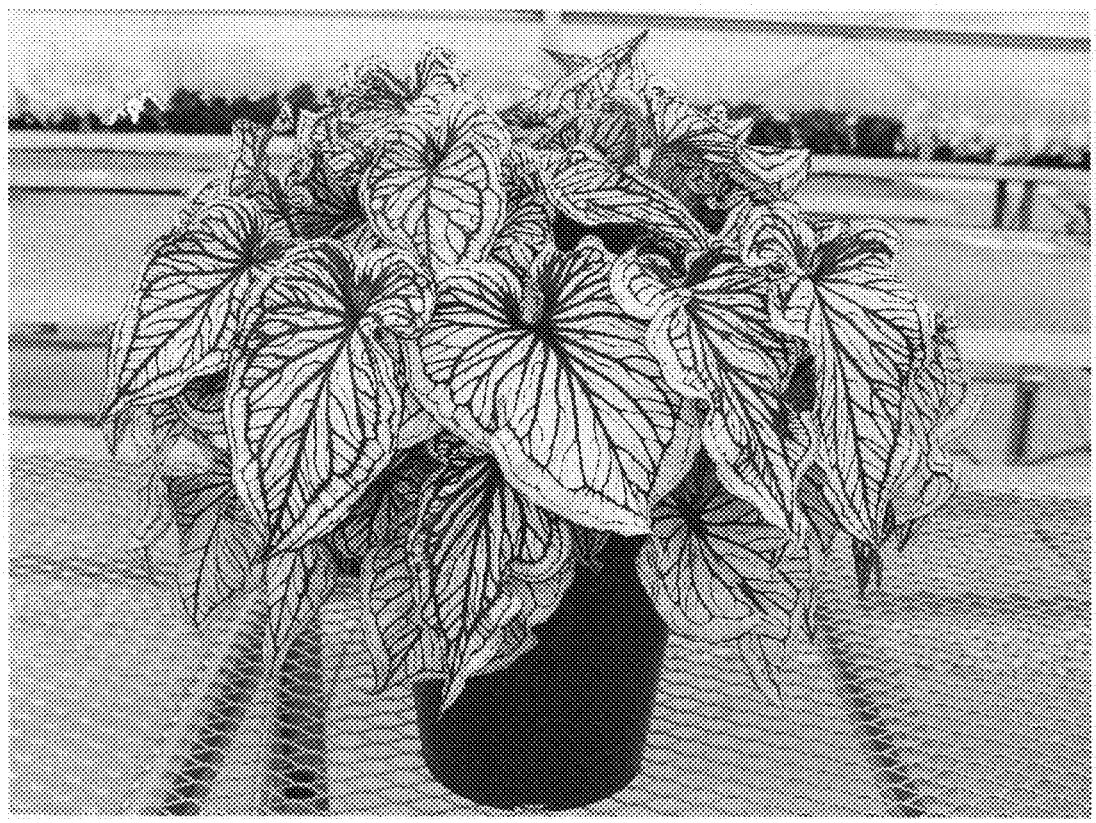

This invention was made with government support under FLA-BRA-04162 awarded by the Cooperative State Research, Education, and Extension Service, USDA. The government has certain rights in the invention.

Genus and species: *Caladium×hortulanum.*

Variety denomination: 'UF331'.

BACKGROUND OF THE NEW PLANT

The invention relates to a new and distinct variety of *Caladium×hortulanum* plant named 'UF331'. 'UF331' originated from a controlled pollination made in 2003 between 'Florida Sweetheart' (U.S. Plant Pat. No. 8,526) and 'Florida Fantasy' (unpatented). 'Florida Sweetheart' was selected as the seed parent because of its multiple leaf development, compact growth habit, high tuber yield, and multiple branching habit. 'Florida Fantasy' was selected as the pollen parent because of its netted venation pattern. Both 'Florida Sweetheart' and 'Florida Fancy' were developed by crosses between 'Candidum Junior' (unpatented) and 'Red Frill' (unpatented). The ancestry of 'Candidum Junior' and 'Red Frill' is unknown, although 'Candidum Junior' was suspected to be a field mutation of 'Candidum' (unpatented). 'UF331' was initially selected in 2004 as GCREC-3220. Asexual propagation of tubers and evaluation in field and pot studies in Wimauma, Fla. since 2004 have shown that the unique features of 'UF331' are stable and reproduced true to type in successive generations of asexual propagation.

Plant Breeder's Rights for this cultivar have not been applied for. 'UF331' has not been made publicly available more than one year prior to the filing of this application.

SUMMARY OF THE INVENTION

*Caladium*[*Caladium×hortulanum* Birdsey, Araceae Juss.] is commonly used as a pot or landscape plant and is valued for its colorful leaves. Commercial caladium plants are grown from tubers. The commercial value of a *caladium* cultivar depends on its tuber yield, leaf color, performance in the landscape as a garden plant, and performance in containers as a pot plant.

The new and distinct variety of *caladium* is a lanced-leaved *caladium* that possesses a novel combination of foliar characteristics. Leaves of 'UF331' are characterized by large, dark green veins and white to pink interveinal areas, producing an attractive coloration pattern. While the leaf face with green veins is similar to the popular fancy-leaved *caladium* 'Candidum Junior' and 'Candidum', 'UF331' is the first lance-leaved variety with this pattern. 'UF331' has improved performance in container forcing and landscape planting compared to other lance-leaved varieties.

DESCRIPTION OF THE PHOTOGRAPHS

This new *caladium* plant is illustrated by the accompanying photographs which show the plant's form and foliage. The new *caladium* has not been observed under all possible environmental conditions. Its phenotype may vary somewhat with variations in the environment such as light intensity and temperature, without, however, any variance in genotype. The colors shown are as true as can be reasonably obtained by conventional photographic procedures. Colors in the photograph may differ slightly from the color values cited in the detailed botanical description, which accurately describe the colors of the new *Caladium.*

FIG. 1 shows the overall plant appearance and habit including foliage from a side perspective view of a typical plant of the new *Caladium* grown in a container.

DESCRIPTION OF THE NEW CULTIVAR

The following detailed description sets forth the distinctive characteristics of 'UF331' with color terminology in accordance with British Color Council and The Royal Horticultural Society, Horticultural Colour Chart, except where general color terms of ordinary dictionary significance are obvious. Wherein dimensions, sizes, and other characteristics are given, it is to be understood that such characteristics are approximations of averages set forth as accurately as practicable. The description herein is from 4 month-old specimens grown in Wimauma, Fla., in 2007. Plants used for describing color were grown in 20.3-cm containers in a 45% shaded greenhouse from four No. 1 (3.8 to 6.4 cm in diameter) tubers.

DETAILED BOTANICAL DESCRIPTION

Classification:

*Botanical.*—*Caladium×hortulanum.*

*Common name.*—*Caladium.*

Parentage:

*Female parent.*—'Florida Sweetheart' (U.S. Plant Pat. No. 8,526) *caladium.*

*Male parent.*—'Florida Fantasy' (unpatented) *caladium.*

Propagation:

*Type.*—By tuber division.

*Time to develop roots and sprout.*—42 days (Spring −15° C. night to 29° C. day). 24 days (Summer −21° C. night to 35° C. day).

*Root description.*—Dense, moderately thick roots (up to 2.5 mm at the basal end) with little branching and few lateral roots.

Plant description:

*Plant shape.*—Mounding, symmetrical.

*Plant height.*—About 29 cm from top of soil to top of leaf plane 4 months from planting tubers in ground beds in full sun.

*Plant width.*—About 25-40 cm 4 months from planting tubers in ground beds in full sun.

*Leaf blade.*—Lanceolate with a saggitate-cordate base and a broad acuminate tip, 22 cm long and 15 cm wide, slightly undulate with green (RHS 137A) penniform venation. The upper surface has dark green (RHS 139A) margins, 1-2 mm wide, bordering the entire leaf except for the basal leaf valley where it is greyed-purple (RHS 187A). The leaf center is greyed-purple (RHS 187A) and up to 20 mm. Leaves have a thick (3 to 5 mm wide) central main vein in dark green (RHS 137A) and numerous (up to 18) large veins (2 to 4 mm wide) in dark green (RHS 137A) radiating from the central vein. These large veins connect marginally with a thinner (1 to 2 mm wide) green vein (RHS 137A) that roughly parallels the leaf margin and the peripheral thin green (RHS 137B) vein. A small green (RHS 137B) vein is located between and parallel to the leaf margin and the peripheral vein. Netted secondary veins are green (RHS 137B). The interveinal area is variable, from white (RHS 155C) to red-purple (RHS 61D), depending on light conditions and leaf maturity, and the area is translucent, making the main veins very prominent. Leaves have a large (approximately 2 cm) greyed-purple (RHS 178A) blotch at the petiole attachment, covering a small portion of the central and large veins. The undersurface has a narrow (1 to 2 mm) greyed-green (RHS 191A) margin. Primary veins are greyed-green (RHS 191). Interveinal areas are variable, greyed white (RHS 156) to red-purple (RHS 61D). The largest leaf on plants grown in a 45% shaded greenhouse produced from an intact No. 1 tuber in an 11.4-cm pot averaged 19 cm long and 13 cm wide 10 weeks after planting. When grown from 2.54-cm tuber propagules in ground beds with full sun, leaves measured approximately 4 months from planting averaged 22 cm long and 12 cm wide.

*Petiole.*—Aspect: Mostly erect, curving outwardly with development. Length: 24.5-29.5 cm. Diameter (distal): 5 mm. Diameter (proximal): 7.5 mm. Strength: Strong, flexible. Color: Black (RHS 202A), with streaks and blotches of greyed-red (RHS 182D). Wing length: 3.5-5 cm. Wing diameter: 7-8.5 mm. Wing color: Black (RHS 202A) with blotches of grey-red (RHS 182D).

*Tuber.*—Jumbo-sized (6.4 to 8.9 cm in diameter) tubers are multi-segmented, bearing 4 to 7 dominant buds. Tuber surfaces are brown (RHS 200B) with the cortical area yellow-orange (RHS 15D). Inflorescence: The inflorescences of 'UF331' have been observed only on shadehouse-grown plants. Inflorescence Arrangement: Upright hooded spathes surrounding a columnar spadix borne on a tall upright scape. Fragrance: None detected. Natural flowering season/longevity: Plants of 'UF331' typically flower during the spring or early summer in central Florida. Flowers develop about seven weeks after growth commences. Inflorescences last about three days before fading; inflorescences persistent.

*Spathe.*—Length: 13.5 cm. Width, distal: 3.5 cm. Width, proximal: 3 cm. Shape: Ovate to somewhat obovate. Apex: Acute to acuminate. Base: Tapering. Margin: Entire; proximal, notched. Texture (upper and lower surfaces): Smooth, glabrous.

*Color.*—Front Surface: Upper two-thirds: yellow-white (RHS 158D), becoming grey-brown (RHS 199D) with maturity; lower one-third: yellow-green (RHS 144A) to yellow-green (RHS 144C). Rear Surface: Upper two-thirds: yellow-green (RHS 145B); lower one-third: yellow-green (RHS 148D) streaked with yellow-green (RHS 147C). Spadix: Spadix with sessile, simple female and male flowers separated into two zones. Female flowers arranged on the lower one-third of the spadix; male flowers arranged on the upper two-thirds of the spadix. Sterile flowers develop between female and male flower zones. Near this area, the spathe constricts surrounding the female flowers. Length (entire spadex): 9.5 cm. Length (male flower zone): 6 cm. Length (sterile flower zone): 1.7 cm. Length (female flower zone): 2 cm. Diameter (male flower zone): 9 mm. Diameter (sterile flower zone): 8 mm. Diameter (female flower zone): 9 mm. Shape: Spindle-shaped to columnar.

*Apex.*—Obtuse.

*Base.*—Obtuse.

*Aspect.*—Upright. Color (mature, male zone): yellow-white (RHS 158B). Color (mature, sterile zone): yellow-white (RHS 158B). Color (mature, female zone): yellow (RHS 11C).

*Male flowers.*—Quantity per spadix: About 230.

*Shape.*—Obovate.

*Height.*—2.5 mm.

*Diameter.*—2 mm. Anther color: RHS 157D. Amount of pollen: Moderate. Female flowers: Quantity per spadix: About 60.

*Shape.*—Obovate.

*Height.*—3 mm.

*Diameter.*—2 mm. Stigma color: RHS 9C. Ovary color: RHS 155D.

*Scape.*—

*Length.*—23 cm.

*Diameter.*—5.5 mm.

*Strength.*—Sturdy, flexible.

*Aspect.*—Erect.

*Texture.*—Smooth, glabrous. Color: Brown (RHS 200A) with streaks and blotches of RHS 199B.

*Seed and fruit.*—No Fruit or Seed without hand pollination.

COMPARISON WITH KNOWN CULTIVARS

Plants of 'UF331' differ from plants of the female parent, 'Florida Sweetheart' (U.S. Plant Pat. No. 8,526), in the following characteristics:

1. Leaves of 'UF331' are more upright and elongated than the leaves of the female parent;
2. Plants of 'UF331' differ from the female parent in leaf coloration as leaves of plants of the female parent have light pink color in the center and pink veins.

Plants of 'UF331' differ from plants of the male parent, 'Florida Fantasy' (unpatented), in the following characteristics:

1. Plants of 'UF331' are shorter than the plants of the male parent;
2. Plants of 'UF331' differ from the male parent in leaf shape as leaves of 'Florida Fantasy' are fancy (or heart) shaped;
3. Plants of 'UF331' differ from the male parent in leaf coloration, as leaves of the male parent have bright red veins.

Additionally, comparisons were made with the commercial varieties 'Florida White Ruffles' (U.S. Plant Pat. No. 14,402), White Wing' (unpatented), and 'Candidum Junior'. 'White Wing' was used for comparison, as it is a popular commercial, white, lance-leaved variety. 'Candidum Junior' was used for comparison as it is a popular commercial, semi-dwarf, fancy-leaved variety with a similar venation and coloration pattern to 'UF331'. Comparisons were made in Wimauma, Fla. in 2006 and 2007.

Field plots were organized in a randomized complete block design consisting of three replications, and each plot contained 30 propagules. Tubers were dug in December 2006 and January 2008, respectively. Dried tubers were graded by maximum diameter, No. 2 (2.5 to 3:8 cm), No. 1 (3.8 to 6.4 cm), Jumbo (6.4 to 8.9 cm), Mammoth (8.9 to 11.4 cm), and Super Mammoth (>11.4 cm). The production index, an indicator of economic value of the harvested tubers, was calculated as: N (No. 2)+2N (No. 1)+4N (Jumbo)+6N (Mammoth)+8N (Super Mammoth); where N=number of tubers in each grade. The average tuber weight of 'UF331' was the same as 'White Wing', but was 1.3× greater than 'Florida White Ruffles' and 1.4× 'Candidum Junior' in 2006 (Table 1). In 2007, 'UF331' had a tuber weight 2.0× to 4.8× greater than the checks. The production index was 1.2× to 2.7× higher for 'UF331' compared to all checks in both 2006 and 2007. 'UF331' produced similar numbers of marketable tubers as 'Florida White Ruffles' and 'White Wing' in both 2006 (49 to 55 tubers) and 2007 (26 to 36 tubers). Compared to 'Candidum Junior', 'UF331' produced a few more tubers (36 vs. 31) in 2007 and significantly more (54 vs. 39) in 2006. The majority (>75%) of marketable tubers produced by 'UF331' were in the No. 1, Jumbo, and mammoth categories. This size distribution is ideal for tubers marketed for container forcing and landscape use.

Landscape performance of the varieties grown under full-sun conditions was evaluated in 2006 and 2007 on the same plots used for evaluating tuber production. The overall plant performance was rated multiple times (July, August, and September) in each growing season, on a scale of 1 to 5, with 1 being very poor (few leaves and lack of vigor), and 5 being excellent (full plants, numerous leaves, and bright color display). Similarly, leaf sun burn tolerance was also evaluated multiple times in each growing season on a scale of 1 to 5, with 1 being very susceptible to sun burns and showing numerous sun-damaged areas or holes on leaves and 5 being resistant to sun burns and not showing any sun-damaged areas. At approximately 4 months after planting, plant height, number of leaves, and foliar characteristics were measured. 'UF331' was significantly taller (5 to 11 cm) and developed significantly larger (4 to 7 cm longer and 2 to 6 cm wider) leaves than 'Florida White Ruffles' and 'White Wing' did (Table 2). 'UF331' performed much better than 'White Wing' during the whole growing season, with much fuller plants and better color display. Compared to 'Florida White Ruffles', the performance ratings of 'UF331' were higher, but the difference was significant only in the early season (July ratings). 'UF331' had excellent tolerance to sun burns during the whole growing season and showed little leaf tissue damage, resulting in the highest ratings.

The varieties' suitability for container forcing was evaluated by forcing tubers in 11.4-cm containers. No. 1 tubers were planted either intact or de-eyed in a peat/vermiculite mix on Mar. 26, 2007. The study was conducted in a greenhouse with 45% light exclusion during the summer in Wimauma, Fla. Average daily temperatures ranged from a low of 16° C. night to 29° C. day during the experiment. Potted plants were arranged on metal benches in the greenhouse in a randomized complete block design with 10 replications. Plant height, number of leaves, and foliar characteristics were recorded 8 to 10 weeks after planting. 'UF331' sprouted in 42 days (intact) or 44 days (de-eyed) after planting, 6 to 9 days later than 'Florida White Ruffles', 9 to 11 days later than 'White Wing', and 10 to 11 days later than 'Candidum Junior' (Table 3). When intact tubers were forced, 'UF331' was 16 cm tall, similar to the three checks; when tubers were de-eyed, 'UF331' was 15 cm, similar to 'Candidum Junior', but 2 to 3 cm shorter than 'Florida White Ruffles' and 'White Wing'. 'UF331' had 7 to 8 leaves on intact plants 10 weeks after planting, but approximately 13 on de-eyed plants. Overall, leaves of 'UF331' were more or less similar to 'Florida White Ruffles', 'White Wing', and 'Candidum Junior' in length and width. 'UF331' produced high quality plants in small pots (11.4 cm in diameter) even without de-eyeing (Table 3).

TABLE 1

Tuber weight, production index, number, and tuber grade distribution of 'UF331' and three commercial cultivars harvested in 2006 and 2007. Values presented are means of three replications with 30 propagules planted in a plot per year.

| | Tuber | | | Tuber distribution[z] (%) | | | | |
|---|---|---|---|---|---|---|---|---|
| Varieties | Weight (kg) | Production index[y] | Marketable (no.) | Super mammoth | Mammoth | Jumbo | No. 1 | No. 2 |
| | Year 2006 | | | | | | | |
| UF331 | 5.7 | 194 | 54 | 2 | 21 | 43 | 22 | 12 |
| Florida White Ruffles | 4.4 | 163 | 55 | 1 | 17 | 26 | 30 | 27 |

TABLE 1-continued

Tuber weight, production index, number, and tuber grade distribution of 'UF331' and three commercial cultivars harvested in 2006 and 2007. Values presented are means of three replications with 30 propagules planted in a plot per year.

| | Tuber | | | Tuber distribution[z] (%) | | | | |
|---|---|---|---|---|---|---|---|---|
| Varieties | Weight (kg) | Production index[y] | Marketable (no.) | Super mammoth | Mammoth | Jumbo | No. 1 | No. 2 |
| White Wing | 5.7 | 164 | 50 | 3 | 13 | 38 | 33 | 13 |
| Candidum Junior | 4.0 | 128 | 39 | 3 | 11 | 50 | 21 | 16 |
| | Year 2007 | | | | | | | |
| UF331 | 4.3 | 109 | 36 | 1 | 10 | 28 | 36 | 16 |
| Florida White Ruffles | 1.0 | 43 | 30 | 0 | 1 | 4 | 27 | 68 |
| White Wing | 0.9 | 41 | 29 | 0 | 0 | 4 | 33 | 63 |
| Candidum Junior | 2.1 | 71 | 32 | 0 | 0 | 26 | 54 | 20 |

[z]Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).
[y]The production index is an indicator of economic value of the crop harvested and is calculated as: N (No. 2) + 2N (No. 1) + 4N (Jumbo) + 6N (Mammoth) + 8N (Super Mammoth), where N = number of tubers in each grade.

TABLE 2

Plant characteristics, performance, and sun tolerance ratings of 'UF331' and three commercial cultivars grown from planting 2.54-cm caladium tuber propagules in ground beds in full sun (2006 and 2007). Values presented for plant height, leaf number, length and width are means of three replications with three plants measured per plot per year, while performance and sun burn tolerance ratings are means of three replications based on whole plot evaluation.

| Varieties | Plant height[z] (cm) | Leaves[z] (no.) | Leaf length[z] (cm) | Leaf width[z] (cm) |
|---|---|---|---|---|
| UF331 | 29 | 23 | 22 | 12 |
| Florida White Ruffles | 18 | 27 | 16 | 8 |
| White Wing | 24 | 20 | 18 | 10 |
| Candidum Junior | 32 | 17 | 23 | 16 |

| | Performance rating[y] | | | Sun tolerance ratings[x] | | |
|---|---|---|---|---|---|---|
| Varieties | July | August | September | July | August | September |
| UF331 | 3.8 | 3.5 | 4.4 | 4.8 | 4.3 | 4.4 |
| Florida White Ruffles | 2.0 | 2.9 | 3.5 | 4.5 | 4.1 | 4.2 |
| White Wing | 2.0 | 2.3 | 2.9 | 4.2 | 4.1 | 4.3 |
| Candidum Junior | — | 2.3 | 3.6 | — | 2.7 | 4.0 |

[z]Data were taken over two growing seasons (2006 and 2007), approximately 4 months (August 2006 and 2007) after tubers were planted in April each year.
[y]Plants were rated on a scale of 1 to 5, with 1 being very poor, 3 fair and acceptable, and 5 being excellent in plant vigor, fullness, and color display, in July, August, and September in 2006 and 2007, respectively.
[x]Plants' sun burn tolerance was rated on a scale of 1 to 5, with 1 being very poor, 3 fair and acceptable, and 5 being excellent without showing any signs of leaf burns or resulted holes on leaf surfaces, taken in July, August, and September in 2006 and 2007, respectively.

TABLE 3

Plant performance for caladium cultivars grown from No. 1 tubers in 11.4-cm containers in a 45% shaded glasshouse, 2007, Wimauma, Fla. Values represent the means of 10 plants produced from intact or de-eyed No. 1 (>3.8 and <6.4 cm in diameter) tubers planted individually per container. Data was taken 8 weeks after planting.

| | Days to sprout[z] | | Plant height (cm) | | Leaves (no.) | |
|---|---|---|---|---|---|---|
| Varieties | Intact | De-eye | Intact | De-eye | Intact | De-eye |
| UF331 | 42 | 44 | 16 | 15 | 8 | 13 |
| Florida White Ruffles | 36 | 36 | 18 | 17 | 11 | 13 |
| White Wing | 31 | 35 | 19 | 18 | 8 | 11 |
| Candidum Junior | 31 | 34 | 19 | 15 | 11 | 10 |

| | Leaf length (cm) | | Leaf width (cm) | | Quality rating | |
|---|---|---|---|---|---|---|
| Varieties | Intact | De-eye | Intact | De-eye | Intact | De-eye |
| UF331 | 19 | 16 | 13 | 10 | 3.9 | 4.4 |
| Florida White Ruffles | 20 | 20 | 11 | 11 | 3.3 | 3.5 |
| White Wing | 19 | 18 | 12 | 9 | 3.2 | 4.0 |
| Candidum Junior | 20 | 18 | 13 | 11 | 3.6 | 3.5 |

[z]Number of days from planting to the first unfurled leaf.

I claim:

1. A new and distinct cultivar of *Caladium* plant as shown and described herein.

* * * * *